(12) United States Patent
Song et al.

(10) Patent No.: US 10,371,853 B2
(45) Date of Patent: *Aug. 6, 2019

(54) NUCLEAR MAGNETIC RESONANCE SYSTEM WITH FEEDBACK INDUCTION COILS

(71) Applicant: SCHLUMBERGER TECHNOLOGY CORPORATION, Sugar Land, TX (US)

(72) Inventors: Yi-Qiao Song, Newton Center, MA (US); Michael Wilt, Walnut Creek, CA (US); Pabitra Sen, Chapel Hill, NC (US)

(73) Assignee: SCHLUMBERGER TECHNOLOGY CORPORATION, Sugar Land, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/659,186

(22) Filed: Jul. 25, 2017

(65) Prior Publication Data

US 2017/0322338 A1    Nov. 9, 2017

Related U.S. Application Data

(63) Continuation of application No. 13/952,999, filed on Jul. 29, 2013, now Pat. No. 9,715,032.

(60) Provisional application No. 61/677,923, filed on Jul. 31, 2012.

(51) Int. Cl.
*G01V 3/32* (2006.01)
*G01N 24/08* (2006.01)
*G01R 33/36* (2006.01)
*G01R 33/3415* (2006.01)
*G01R 33/44* (2006.01)

(52) U.S. Cl.
CPC ............... *G01V 3/32* (2013.01); *G01N 24/08* (2013.01); *G01R 33/3621* (2013.01); *G01N 24/081* (2013.01); *G01N 24/085* (2013.01); *G01R 33/3415* (2013.01); *G01R 33/445* (2013.01)

(58) Field of Classification Search
CPC .. G01V 3/32; G01R 33/3621; G01R 33/3415; G01N 24/085
See application file for complete search history.

(56) References Cited

U.S. PATENT DOCUMENTS

| | | | | |
|---|---|---|---|---|
| 4,792,757 A | * | 12/1988 | Vail, III | G01R 33/022 324/303 |
| 7,532,007 B2 | * | 5/2009 | Song | G01V 3/32 324/303 |
| 2009/0058416 A1 | * | 3/2009 | Blanz | G01N 24/081 324/303 |

* cited by examiner

*Primary Examiner* — Gregory H Curran (57) ABSTRACT

A nuclear magnetic resonance (NMR) system that uses a feedback induction coil to detect NMR signals generated within a substance is described herein. In one embodiment, the NMR system uses the Earth's magnetic field in conjunction with a transmitter coil that applies NMR sequences to a formation. The NMR sequences generate a weak NMR signal within the formation due to the weakness of the Earth's magnetic field. This weak NMR signal is detected using the feedback induction coil.

20 Claims, 9 Drawing Sheets

NUCLEAR MAGNETIC RESONANCE SYSTEM WITH FEEDBACK INDUCTION COILS

PRIORITY

The present application claims the benefit of U.S. Application Ser. No. 61/677,923, filed Jul. 31, 2012, which application is incorporated herein, in its entirety, by reference.

TECHNICAL FIELD

This disclosure relates to nuclear magnetic resonance (NMR), and more particularly to using NMR to determine the properties of substances.

BACKGROUND

Nuclear magnetic resonance (NMR) can be used to determine properties of a substance. Oil and gas field tools use NMR systems to investigate the properties of earth formations, such as the porosity of formations or the composition of fluids within the formations. In one example, the NMR system is lowered into a wellbore that traverses a formation. The NMR system can be lowered into the wellbore as part of a wireline or drilling string. The NMR system is used to investigate the properties of the formation adjacent to the wellbore. The system includes a magnet for applying a static magnetic field to the formation adjacent to the wellbore. The system also includes a coil for applying an oscillating magnetic field to the formation adjacent to the wellbore. The oscillating field is composed of a sequence of pulses that tip the magnetization of the atomic nuclei within the formation away from an initial magnetization produced by the magnet. The sequence of pulses and the static magnetic field interact with the nuclei in a manner such that a NMR signal composed of "echoes" is generated within at least a portion of the formation. The NMR signal within the formation is detected using the coil and used to determine the properties for the formation.

Due to the weak magnetic field produced by the magnet and the limited sensitivity of the coil, the depth of investigation of such wellbore NMR systems is limited. For example, in some cases, the depth of investigation is between 2 and 10 cm. Also, the static field applied to the formation is inhomogeneous because the field decreases in strength as a function of distance from the magnet. Because of this inhomogeneous field, the NMR signal is produced in a small portion of the formation. This small portion is known as a "shell." In some cases, the shell has a volume of $10^{-4}$ $m^3$ (100 cc). Accordingly, to investigate a large area, the NMR system determines the properties of multiple shells. Investigating multiple shells is time consuming and is a particular problem in wireline or drilling applications where time is costly.

SUMMARY

Illustrative embodiments of the present disclosure are directed to a NMR system that includes a feedback induction coil that detects NMR signals generated within a substance. In various embodiments, the feedback induction coil provides improved sensitivity over past receiver coils. In one specific embodiment, the NMR system uses the Earth's magnetic field in conjunction with a transmitter coil that applies NMR sequences to a formation. The NMR sequences generate a weak NMR signal within the formation due to the weakness of the Earth's magnetic field. The sensitivity of the feedback induction coil provides for detection of this weak NMR signal, while also improving the NMR system's depth of investigation (DOI) into the formation.

In some embodiments, a wellbore tool includes both the feedback induction coil and the transmitter coil. In other embodiments, the wellbore tool includes the feedback induction coil, while a surface module includes the transmitter coil. In yet another embodiment, a surface module includes both the feedback induction coil and the transmitter coil.

Various embodiments of the present disclosure are also directed to a method for analyzing a substance using NMR. The method includes applying an NMR pulse sequence to the substance and detecting NMR signals generated within the substance by the NMR pulse sequence using a feedback induction coil. In some embodiments, the NMR signals are generated using a magnetic field of the Earth as a static magnetic field.

Illustrative embodiments of the present disclosure are directed to a wellbore tool. The tool includes a transmitter coil that applies a NMR sequence to a substance and a feedback induction coil configured to detect NMR signals generated within the substance.

BRIEF DESCRIPTION OF THE DRAWINGS

Those skilled in the art should more fully appreciate advantages of various embodiments of the disclosure from the following "Description of Illustrative Embodiments," discussed with reference to the drawings summarized immediately below.

DESCRIPTION OF ILLUSTRATIVE EMBODIMENTS

Illustrative embodiments of the present disclosure are directed to a nuclear magnetic resonance (NMR) system that uses a feedback induction coil to detect resonant NMR signals generated within a substance. In various embodiments, the feedback induction coil provides improved sensitivity over past receiver coils. In one specific embodiment, the NMR system uses the Earth's magnetic field in conjunction with a transmitter coil that applies NMR sequences to a formation. The NMR sequences generate a weak NMR signal within the formation due to the weakness of the Earth's magnetic field. The sensitivity of the feedback induction coil provides for detection of this weak resonant NMR signal, while also improving the NMR system's depth of investigation (DOI) into the formation. Details of various embodiments are discussed below.

Figure 1:
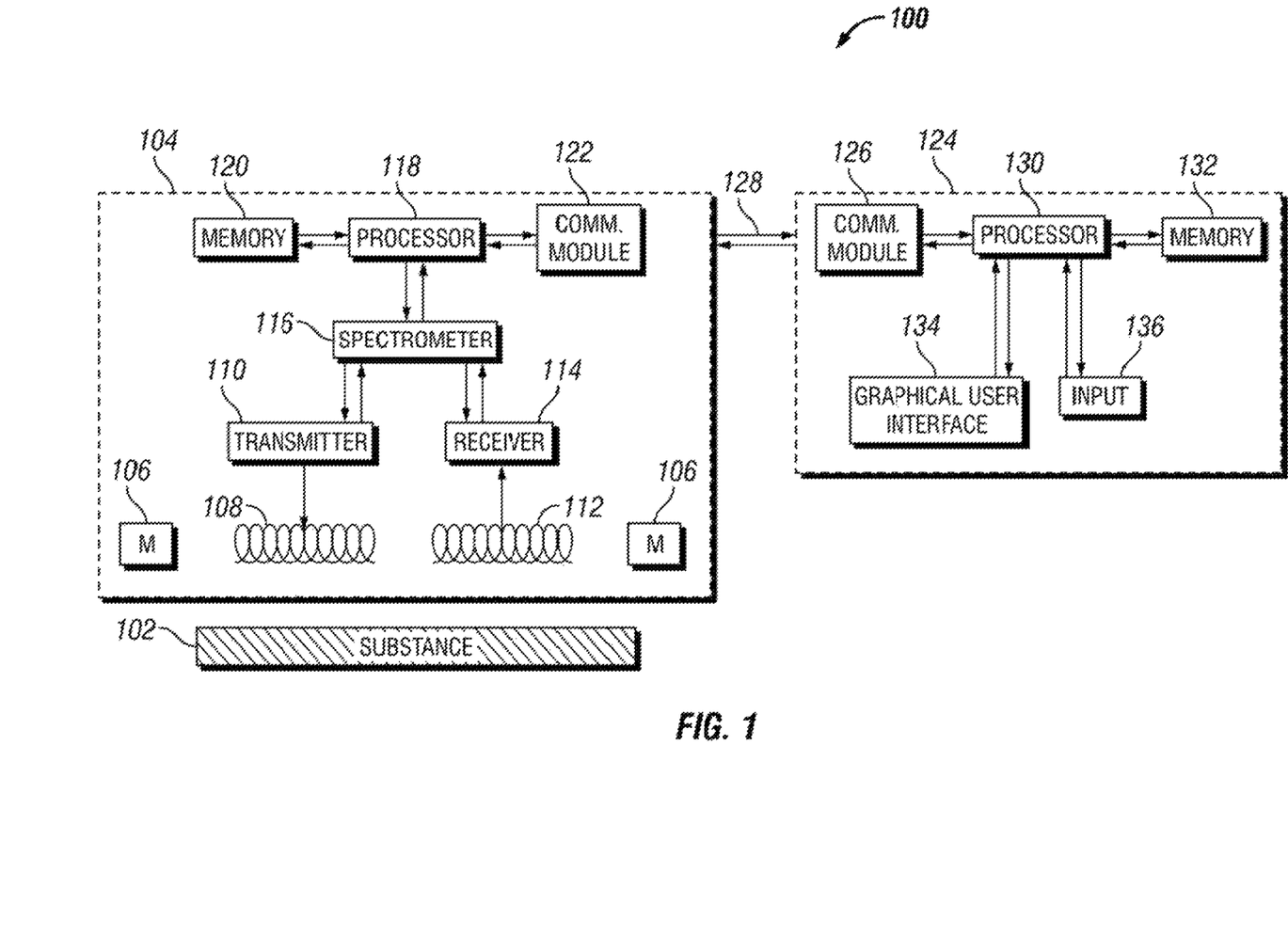
FIG. 1 shows a nuclear magnetic resonance (NMR) system for analyzing a substance in accordance with one embodiment of the present disclosure.

FIG. 1 shows a NMR system 100 for analyzing a substance 102. The system 100 includes an NMR module 104 that includes an electro-magnetic device 106 for applying a static magnetic field to the substance 102. The static magnetic field is referred to as $B_0$. In some embodiments, the electro-magnetic device 106 is a magnet or an array of magnets. The magnets can be formed from a samarium-cobalt (SmCo) magnetic material.

The NMR module 104 also includes a transmitter coil 108 (e.g., antenna) for applying an oscillating magnetic field (e.g., a radio frequency (RF) field) to the substance 102. The oscillating magnetic field is referred to as Bi. The transmitter coil 108 is coupled to a NMR transmitter 110, which drives current through the transmitter coil 108 and, in turn, generates the oscillating magnetic field. The oscillating magnetic field is defined by a series of pulses known as an NMR pulse sequence. Each pulse sequence includes a series of RF pulses. Each pulse is defined by duration (e.g., pulse length), amplitude (e.g., magnitude of the current in the transmitter coil), phase, frequency, and time delay between the pulses. These parameters are controlled by an operator module and spectrometer, as further described below. In one specific example, the NMR pulse sequence is a Carr, Purcell, Meiboom and Gill (CPMG) sequence. In various other embodiments, the pulse sequence can be a spin echo, free-induction decay, inversion recovery, saturation recovery, and/or stimulated echo sequence. The NMR pulse sequences are applied at the Larmor frequency of a certain set of nuclei within the substance 102 (e.g., hydrogen or sodium nuclei) to manipulate the spins of nuclei within the substance and to cause the nuclei to generate a NMR signal (e.g., a spin precession signal).

Figure 2:
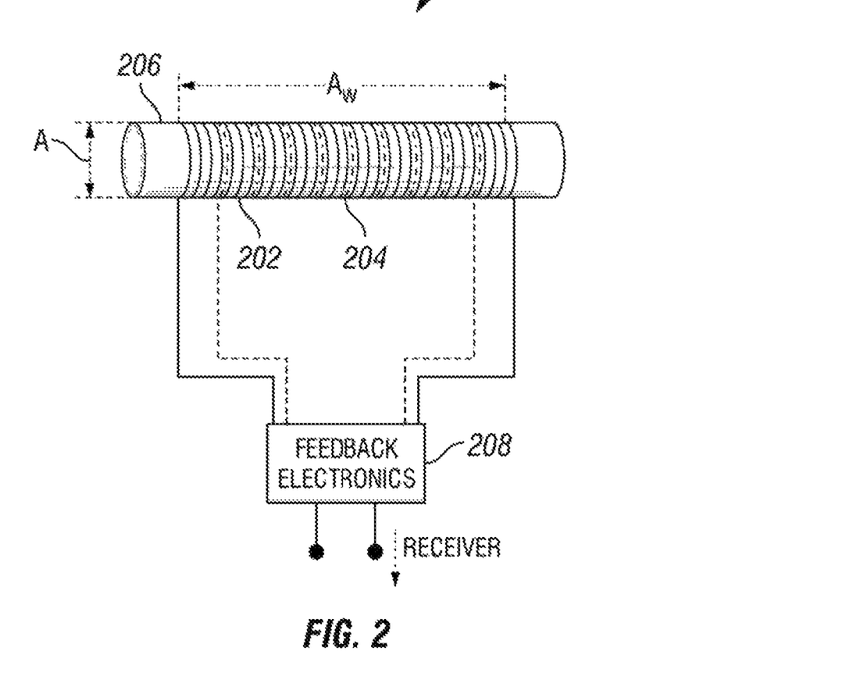
FIG. 2 shows a feedback induction coil in accordance with one embodiment of the present disclosure.

The NMR module 104 includes a receiver coil 112 coupled to an NMR receiver 114 for detecting the NMR signal that is generated by the transmitter coil 108 within the substance 102. In various embodiments, the NMR signal is acquired by the receiver coil 112 after the NMR pulse sequences have been applied to the substance 102 (e.g., during detection). The receiver coil 112 is a feedback induction coil. FIG. 2 shows a feedback induction coil 200 in accordance with one embodiment of the present disclosure. In this embodiment, the feedback induction coil 200 is a solenoid coil that includes a primary coil 202 and a feedback coil 204. The primary coil 202 and the feedback coil 204 are wound around a core 206. In various embodiments, the core 206 includes a magnetically permeable material, such as a mu-metal (μ-metal). In one specific embodiment, the core 206 is formed from a bundle of mu-metal strips. In various embodiments, the primary coil 202 includes more turns than the feedback coil 204. For example, in one embodiment, the primary coil 202 includes 10,000 turns, while the feedback coil includes 200 turns.

The magnetic feedback induction coil 200 also includes feedback electronics 208 that are coupled to the primary coil 202 and the feedback coil 204. The feedback electronics 208 are configured to produce an output current that is applied to the feedback coil 204. The feedback current is set so that the current cancels the magnetic field through the primary coil 202. The primary coil 202 is used as a null detector. When the magnetic field through the primary coil 202 is cancelled, the feedback current that is sufficient to cancel the magnetic field is linearly proportional to the magnetic field that is applied to the primary coil from resonant NMR signals generated in the substance 102. Accordingly, in this manner, the feedback current applied to the feedback coil 204 can be used to measure and determine resonant NMR signals (e.g., amplitude of the signals). In some embodiments, this feedback current is provided to the NMR receiver 114 as a voltage signal. For example, the feedback current can be applied across a resistor within the feedback electronics 208. The voltage across the resistor will be proportional to the feedback current. The voltage across the resistor can be used by the NMR receiver 114 as representative of the NMR signal and this voltage signal can undergo amplification and further processing by the receiver.

In an embodiment of the present disclosure, the primary coil 202 has a large moment. For example, when the transmitter coil 108 is located at a surface location, the primary coil 202 has a moment of at least 200,000 A-m². In another example, when the transmitter coil 108 is located within the wellbore, the primary coil 202 has a moment of at least 1,000 A-m². The moment (M) of a coil can be calculated using the following relationship:

$$M = A * N * \mu \qquad (1)$$

where A is the cross-sectional area of the coil, N is the number of turns on the coil, and μ is the permeability of the coil. In some embodiments, the primary coil 202 includes at least 100 turns. To achieve a larger moment, in other embodiments, the primary coil 202 has at least 1000 turns. In yet another embodiment, the primary coil 202 has at least 20,000 turns. In additional or alternative embodiments, the primary coil 202 has a permeability (μ) of at least 1000. Also, in various illustrative embodiments, the primary coil 202 has a cross-sectional area (A) no greater than 400 cm². Furthermore, in one example, the feedback induction coil 200 has a winding area ($A_w$) of about 45 cm.

FIG. 2 shows a feedback induction coil 200 with a single primary coil 202 and a single feedback coil 204. In other embodiments, the feedback induction coil includes an array of primary coils and an array of feedback coils. Further details regarding magnetic feedback induction coils can be found in U.S. Pat. No. 5,130,655 issued on Jul. 14, 1992, which is hereby incorporated by reference in its entirety.

Figure 3:
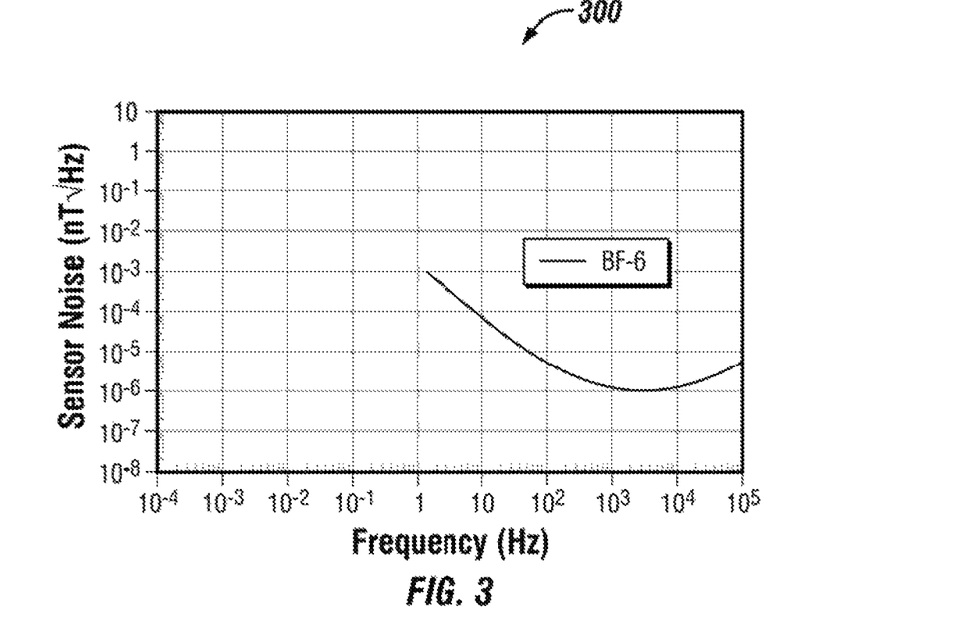
FIG. 3 shows a plot of noise level versus frequency for a magnetic feedback induction coil.

In some embodiments, the feedback induction coil is sufficiently sensitive to detect the NMR signal produced within the substance by the transmitter coil and the Earth's magnetic field. To this end, in various embodiments, the feedback induction coil has a sensitivity of at least 1 fT/√Hz (1 fT=$10^{-6}$ nT) within a range between 1 kHz to 10 kHz. The Larmor frequency of the Earth's magnetic field is approximately 2 kHz and within this high sensitivity range. The 1 fT/√Hz sensitivity is sufficient to detect the resonant NMR signal produced in the substance. Such feedback induction coils are commercially available from Schlumberger Technology Corporation of Sugarland, Tex. FIG. 3 shows a plot 300 of noise floor of 1 fT/√Hz within a range between 1 kHz to 10 kHz for a BF-6 geophysical magnetic feedback induction coil from Schlumberger Technology Corporation.

As shown in FIG. 1, the NMR module 104 also includes a spectrometer 116 that is used to provide NMR pulse sequences to the NMR transmitter 110 and to analyze the NMR signal received from the NMR receiver 114. In various embodiments, the detected NMR signal is output by the NMR receiver 110 in analog form. In such embodiments, the spectrometer 116 may include a digitizer for converting the detected NMR signal into digital data. Furthermore, in various embodiments, demodulation of the NMR signal can occur within the spectrometer 116. In various other embodiments, however, demodulation of the NMR signal can also occur within the NMR receiver 114. The spectrometer 116 also includes a post-processor that is used to interpret the detected digital resonant data and to determine NMR properties from the detected data. This data can be presented to a user using an operator module 124 with a graphical user interface (GUI) 134. In various embodiments of the present disclosure, the operator module 124 and the graphical user interface 134 are not part of the spectrometer 116. The spectrometer 116 also includes a pulse sequence generator. The pulse sequence generator generates NMR pulse sequences based upon parameters selected by an operator at the operator module 124. The pulse sequence generator provides the sequences to the NMR transmitter 110. In one particular embodiment, the spectrometer 116 is a KEA™, which can be obtained from Magritek of Aachen, Germany. The spectrometer 116 can be controlled from the operator module using PROSPA™ software, which can also be obtained from Magritek.

The spectrometer 116 is electronically coupled to a processor 118 and a memory 120 (e.g., a computer system). The memory 120 can be used to store computer instructions (e.g., computer program code) that are interpreted and executed by the processor 118. The memory 120 may be a digital memory such as a random-access memory, a flash drive, a hard drive, or a disc drive.

In various embodiments, the NMR pulse sequences may be implemented as a series of computer instructions fixed either on a non-transitory tangible medium, such as a computer readable medium (e.g., a diskette, CD-ROM, ROM, field-programmable array (FPGA) or fixed disk) or transmittable to a computer system, via a modem or other interface device, such as a communications adapter connected to a network over a tangible medium (e.g., optical or analog communications lines). The series of computer instructions can embody all or part of the NMR pulse sequences described herein.

The NMR pulse sequences may be stored within the memory 120 as software or firmware. The processor 118 may be configured to retrieve the sequences from the memory 120 and provide instructions to the spectrometer 116 to apply the sequences to the substance 102. The detected NMR signals may also be communicated from the spectrometer 116 to the processor 118 for storage on the memory 120.

The processor 118 is also electronically coupled to a communications module 122. The communications module 122 communicates with the operator module 124. The operator module 124 also includes a communications module 126 so that the operator module 124 can communicate with the NMR module. A communications link 128 between the operator module 124 and the NMR module 104 can be established using, for example, a hard-wired link, an optical link, acoustic link, and/or a wireless link.

The operator module 124 includes a processor 130 and a memory 132 (e.g., a computer system). The processor 130 and memory 132 support the graphical user interface (GUI) 134, such as a monitor, a touch screen, a mouse, a keyboard and/or a joystick. The graphical user interface 134 allows an operator to control and communicate with the NMR module. The processor 130 is also electronically coupled to one or more information input devices 136. In some embodiments, the input device 136 is a port for communicating with a removable medium (e.g., a diskette, CD-ROM, ROM, USB and/or fixed disk). In additional or alternative embodiments, the input device 136 is a modem and/or other interface device that is in communication with a computer network (e.g., Internet and/or LAN). In various embodiments, the NMR module 104 and the operator module 124 can be used to perform functions selected from the following non-limiting list:

Communicate instructions to the NMR module 104 to initiate and/or terminate NMR measurements;
Communicate instructions to change parameters of NMR sequences to the NMR module 104 (e.g., pulse duration, pulse amplitude, phase, time delay between pulses, shape of pulses, and/or frequency of pulses);
Communicate detected NMR signal data from the NMR module 104 to the operator module 124;
Communicate NMR pulse sequences from the operator module 124 to the NMR module 104;
Perform analysis of detected NMR signal data to determine NMR properties of substances at the operator module 124 and/or the NMR module 104;
Display various plots of NMR properties to the operator at the operator module 124 using the graphical user interface 134;
Download NMR pulse sequences from the operator module 124 to the NMR module 104;
Sync the operation of the components of the NMR system 100 (e.g., transmitter coil, receiver coil, transmitter, receiver);
Initiate and cease data acquisition by the receiver 114;
Modulate receiver phase and gain; and
Direct operation of a duplexer, as described further below to protect (e.g., blank) the receiver 114 during transmission mode.

Illustrative embodiments of the present disclosure are not limited to the system 100 shown in FIG. 1. Various modifications can be made to the system. For example, in one specific embodiment, the feedback induction coil 114 is used as both the transmitter coil and the receiver coil. In such an embodiment, the feedback induction coil 114 is coupled to both the transmitter 110 and the receiver 114. The NMR module 104 may include a duplexer for coupling the feedback induction coil 112 from the receiver 114 during a detection period and decoupling the coil from the receiver when the NMR pulse sequences are being applied to the substance 102. In another example, the NMR module 104 lacks the electromagnetic device. In some embodiments, the Earth's magnetic field is used as the static field. In such embodiments, the NMR system 100 may not include an electro-magnetic device 106. In yet another example, the NMR module 104 lacks the processor 118 and the memory 122. In such an embodiment, the processor 130 and memory 132 on the operator side support the spectrometer 116. Furthermore, in various embodiments, the NMR module 104 and the operator module 124 can be physically located in the same place as a single system. This may be the case when the system 100 is used in a surface environment, such as a laboratory. In some other embodiments, the NMR module 104 and the operator module 124 can be physically located in two separate locations. For example, in a wellbore application, the NMR module 104 can be located in the wellbore, while the operator module 124 is located at the surface.

The NMR system 100 described in FIG. 1 has many applications. For example, the NMR system can be used to analyze subterranean formation in oil and gas resource development, oil and gas field exploration, hydrology, shallow subsurface contamination monitoring, ground water contamination monitoring, mineral exploration, and/or civil engineering.

Figure 4:
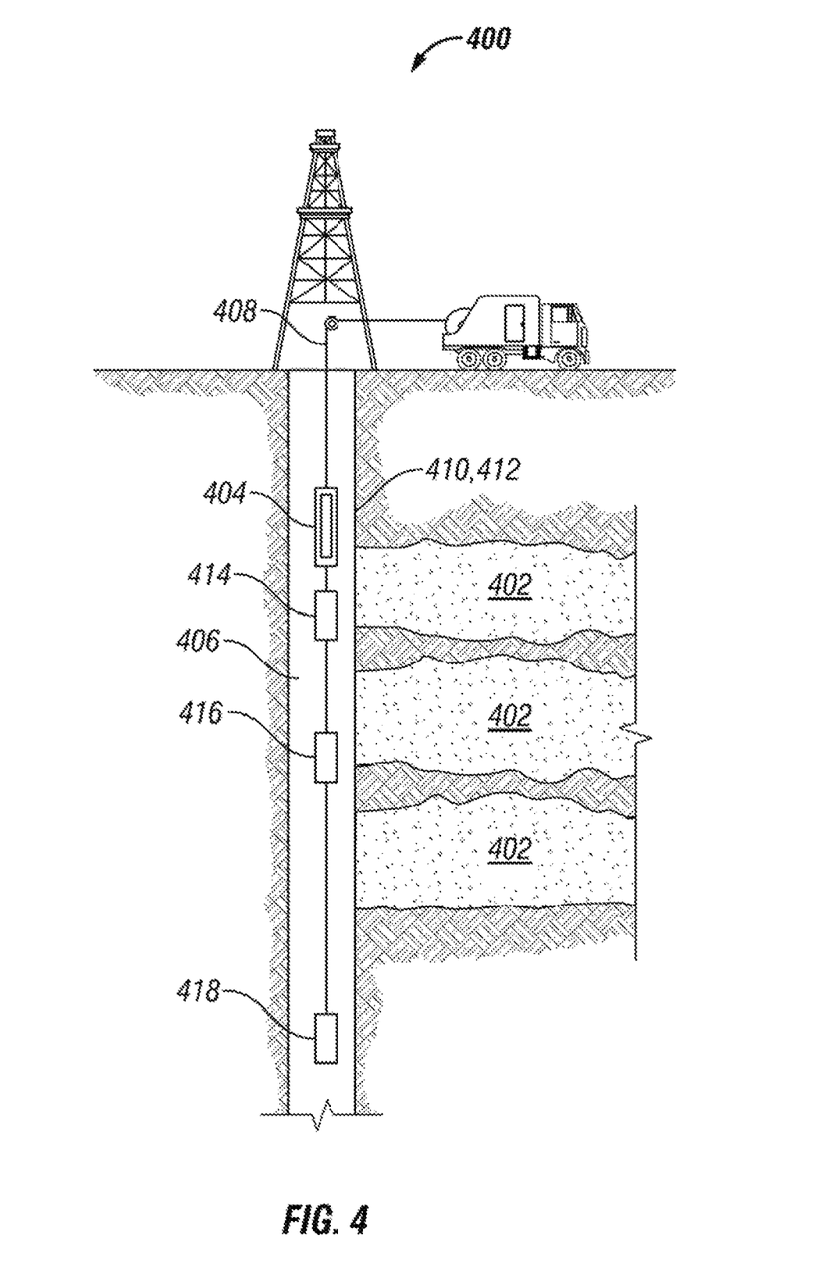
FIG. 4 shows a NMR system deployed as part of a wellbore system in accordance with one embodiment of the present disclosure.

FIG. 4 shows one implementation of the NMR system. In particular, the figure shows a NMR system deployed as part of a wellbore system 400 for investigating a subsurface formation 402 and determining the properties of the subsurface formation near the wellbore. The wellbore system 400 includes a wellbore tool 404 that is disposed within a wellbore 406 that traverses the subsurface formation 402. The wellbore tool 404 is disposed on an armored cable 408. In this example, the wellbore tool 404 is a wireline tool (e.g., a wireline tool string). The wellbore tool 404 includes a NMR transmitter module 410 that includes a transmitter coil 412 for applying an NMR pulse sequence to the formation 402. The pulse sequences applied to the formation 402 may include free-induction decay, spin echo, CPMG, and/or inversion recovery sequences. The pulse sequences can be used to measure spin relaxation and/or diffusion properties of fluids within the formation 402. Such pulse sequences are used in NMR laboratory experiments and NMR well-logging, such as logging-while-drilling applications.

The dimensions of the transmitter coil 412 are limited by the dimensions of the wellbore tool 404 and the wellbore itself 406. In various embodiments, the transmitter coil 412 includes a number of turns (e.g., 1, 10, or 100 turns). Furthermore, the coil 412 has a rectangular shape with a width dimension of between 10 to 30 cm and a length dimension of between 0.5 to 3 meters. In one specific example, the transmitter coil 412 has a cross section no greater than 400 cm². The transmitter coil 412 may also include a core. The turns of the transmitter coil 412 are wound around the core, which may include ferrite, powdered iron, and/or a mu-metal material. The transmitter coil 412 may have less turns and a reduced core with less magnetic material and/or lower magnetic permeability, as compared to the feedback induction coils described below, because a large amount of current can be applied to the transmitter coil in order to generate the oscillating magnetic field. With a lower inductance transmitter coil, a lower voltage may be used to generate sufficient current.

The transmitter module 410 also includes a transmitter circuit and a power amplifier for applying an oscillating current to the transmitter coil 412. The transmitter circuit generates the oscillating current and the amplifier amplifies the current before the current is applied to the transmitter coil 412. Such transmitter circuits and amplifiers are known in the art. U.S. Publication No. 2012/0001629 published on Jan. 5, 2012 shows one example of a transmitter circuit. This publication is incorporated herein, in its entirety, by reference. The oscillating current is applied to the coil 412 so that the oscillating magnetic field is generated within the formation 402. In various embodiments, the current applied to the coil is between 5 to 20 Amps. In some embodiments, the current is between 500 and 1000 Amps. In embodiments where a magnet is used to apply the static field, the frequency of the oscillating field may be between 2 MHz to 200 kHz. In embodiments where the Earth's magnetic field is used, the frequency of the oscillating field may be between 1.0 and 2.2 kHz. The specific frequency used will depend on the Earth's magnetic field, which varies depending on location. In illustrative embodiments, the transmitter coil 412 and transmitter circuit are capacitively tuned and matched to the local Larmor frequency of the formation 402. In this manner, the transmitter coil 412 and transmitter circuit are tuned and matched for efficient power transmission. The transmitter module 410 can use transformer-based or capacitor-based impedance transformation to match the impedance of the transmitter circuit closely to that of the power amplifier. Transformer-based or capacitor-based impedance transformation provides for efficient power transformation. Such tuning and matching arrangements are commonly used in the NMR and magnetic resonance imaging (MRI) arts. A parameter that characterizes the strength of the transmitter coil 412 is the dipole moment. The dipole moment is the product of (i) number of turns in the transmitter coil, (ii) the current within the transmitter coil, and (iii) the cross-sectional area of the transmitter coil. In one example, at a frequency of 2.1 KHz, the transmitter coil 412 generates a dipole moment of 1,000 A-m² or greater. The transmitter coil 412 and transmitter circuit can be similar in design to commercially available transmitters used in cross-well electromagnetic systems, as described in, for example, Luis Depavia et al., Next-Generation Crosswell EM Imaging Tool, SPE 116344 (2008).

In the embodiment shown in FIG. 4, the Earth's magnetic field is used as the static magnetic field (e.g., $B_0$). The Earth's magnetic field has a strength of approximately 0.5 G and the precession of proton spin magnetization (e.g., of protons such as from water and oil) in the magnetic field is approximately 2.1 kHz. Although the Earth's magnetic field varies globally, over any large volume near the measurement point, the magnetic field is very uniform. The local geochemical and mineral composition variations, such as the presence of magnetite and other magnetic minerals, could cause some change in the local magnetic field at the level of parts-per-million to parts-per-thousand. Even with these compositional variations, the magnetic field within the formation near the wellbore will be substantially uniform and the NMR signal bandwidth generated within this volume will be quite narrow. In turn, this narrow bandwidth means that a large volume of the formation will produce signal at this narrow frequency band. As a result, the sample volume that is detected using the NMR system can be between 1 and 100 m³ and the depth of investigation can be between 1 to 10 meters, which is an improvement over past NMR tools.

To apply the NMR pulse sequences at an appropriate Larmor frequency, the NMR system may also include a device to measure the direction and magnitude of the Earth's magnetic field. The local Larmor frequency will depend on the magnitude of the Earth's magnetic field. A Hall probe or magnetometer can be used to measure the direction and magnitude of the Earth's magnetic field. The Hall probe or magnetometer can be located in, for example, the transmitter module 410.

The wellbore tool 404 also includes at least one receiver module for detecting the NMR signal generated within the formation 402. In the example of FIG. 4, the wellbore tool 404 includes three receiver modules, 414, 416, 418 separated by 2, 5, and 10 meters, respectively, from the transmitter module 410. In various embodiments, the receiver modules 414, 416, 418 are placed 1 to 10 meters from the transmitter module 410. By separating the receiver modules 414, 416, 418, the receiver modules investigate different parts of the formation 402. Also, the different separation distances allow the system to investigate different depths into the formation (e.g., different depths of investigation). The depth of investigation increases as the separation distance between the transmitter module 402 and a receiver module increases 414, 416, 418. In some embodiments, the depth of investigation can be greater than 10 meters.

The receiver modules 414, 416, 418 also includes at least one receiver coil for detecting the NMR signal. In various embodiments, the receiver coil is a feedback induction coil that is sufficiently sensitive to detect the NMR signal produced within the formation by the transmitter coil 412 and the Earth's magnetic field. The feedback induction coil is particularly well suited for wellbore operation because the coil can operate at high temperatures, in contrast to other technologies, such as superconducting quantum interference devices (SQUID), which use superconducting coils and operate at very low temperatures.

Figure 5:
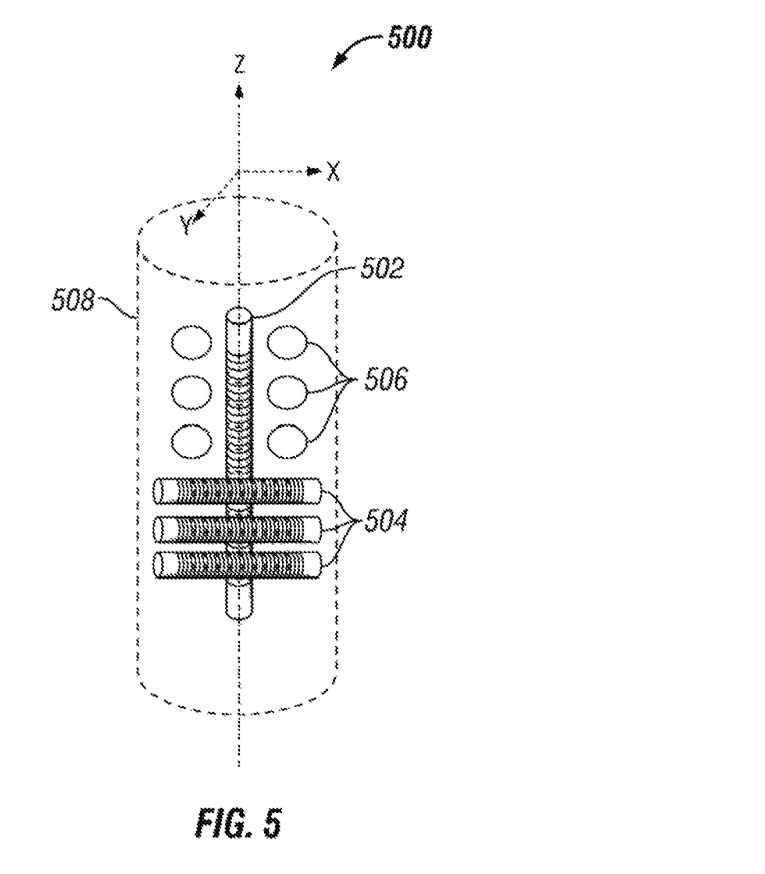
FIG. 5 shows a receiver module with three induction feedback coils in accordance with one embodiment of the present disclosure.

In some embodiments, the receiver modules 414, 416, 418 include a single feedback induction coil. In other embodiments, to increase the sensitivity of the receiver modules in multiple directions 414, 416, 418, the receiver module include a plurality of induction feedback coils. For example, FIG. 5 shows a receiver module 500 that includes three induction feedback coils 502, 504, 506 disposed within a housing 508 (e.g., of the wellbore tool). The geometry of the coils and their core materials determines the sensitivity of the coil to the orientation of the magnetic field. For example, a solenoid coil, such as the one shown in FIG. 2, is sensitive to magnetic fields along the axial direction of the coil. To increase the sensitivity of the receiver module 500 to multiple different directions, the receiver module includes a plurality of coils that are oriented in different directions. As shown in FIG. 5, the induction feedback coils 502, 504, 506 are oriented along the x-axis (504), the y-axis (506), and the z-axis (502). The z-axis corresponds with the axis of the wellbore tool 404. In various embodiments, the housing 508 (e.g., of the wellbore tool) has a diameter of 10 cm or less. To preserve the sensitivity of the coils aligned along the x-axis (504) and the y-axis (506), the coils are composed of a plurality of shorter components. Wellbore tools are less constrained in the vertical directions. Accordingly, in some embodiments, the feedback induction coil aligned along the z-axis (502) is composed of a single component. Such a three-axis coil system measures the full vector of the magnetic field. Furthermore, in various embodiments, such a three-axis coil system improves signal-to-noise and provides more robust operation in different wellbore deviations and local Earth magnetic field orientations.

In illustrative embodiments, the measured signal from each feedback induction coil 502, 504, 506 is combined. In some embodiments, the measured signals are combined by coupling the coils in series. In other embodiments, the signals can be detected separately by the coils 502, 504, 506 and recombined digitally using signal processing or data analysis. The gain of each coil can be determined dynamically based on the orientation of the Earth's magnetic field relative to the wellbore axis in order to maximize reception of the NMR signal. One way to take advantage of the three axis coil system is to combine the three signals from each axis with an appropriate gain so that a sum of the signals corresponds to an effective coil that is perpendicular to the magnetic flux of the NMR signal. In this manner, the reception of the NMR signal is maximized. The three-axis coil can be dynamically adjusted to maximize the signal reception (e.g., as the wellbore orientation changes). For example, if the detected magnetic flux is in the x-y plane and 45 degrees from the x and y axes, then a gain coefficient for the x-axis coil and the y-axis coil will be sqrt(2)/2, while a gain coefficient for the z-coil will be zero. The receiver module 500 may also include one or more integrated pre-amplifiers for amplifying the signals generated by the coils 502, 504, 506.

In some embodiments, the receiver module 500 and its feedback induction coils 502, 504, 506 are protected from pulses of the oscillating magnetic field produced by the NMR system. The sensitive array of feedback induction coils could become over-saturated when the NMR system is applying the strong NMR pulses to the formation. For this reason, in various embodiments, NMR signals are detected when the NMR system is not applying the oscillating field. Also, to allow the receiver module 500 and supporting electronics (e.g., receiver and spectrometer) to receive the NMR signal without interference, the receiver module is protected (e.g., blanked) when the transmitter coil is operating in a transmission mode. There are a number of ways to protect the receiver module 500. In a first embodiment, a winding is installed on each feedback induction coil 502, 504, 506. The winding is wound in opposition to the primary coil and the winding uses a portion of the current from a transmitter pulse to cancel the field induced within the primary coil. In a second embodiment, a compensating coil (e.g., bucking coil) is positioned midway between a transmitter coil and the feedback induction coils 502, 504, 506. This compensating coil is wound and positioned in a way that reduces or eliminates the oscillating magnetic field at the receiver coils during transmission.

In additional embodiments, the receiver module 500 may also include a duplexer that temporarily turns off at least part of a receiver that is coupled to the feedback induction coils 502, 504, 506. The duplexer may include a circuit with electronic switches (e.g., metal-oxide field effect transistors (MOSFET)) that isolate the receiver from the receiver coils 502, 504, 506. The duplexer reduces saturation within the receiver and other supporting electronics. After the NMR pulse sequences are executed, but before the detection of the NMR signal, the receiver is turned back on using the duplexer. Furthermore, in various embodiments, cross-diodes are applied to the frontend of the receiver to limit the potentially large voltage developed over the receiver coil.

As shown in FIG. 4, the wellbore system 400 also includes surface equipment 420 for supporting the wellbore tool 404 within the wellbore 406. In this case, the surface equipment 420 includes a truck that supports the wireline tool 404. In another embodiment, however, the surface equipment 420 may be located within a cabin on an off-shore platform. In various embodiments, the surface equipment 420 includes a power supply for providing electrical power to the wellbore tool 404. The surface equipment 420 also includes an operator interface for communicating with the NMR transmitter module 410 and receiver modules 414, 416, 418 through, for example, the armored cable 408. Such an operator interface has already been described with reference to FIG. 1.

Figure 6:
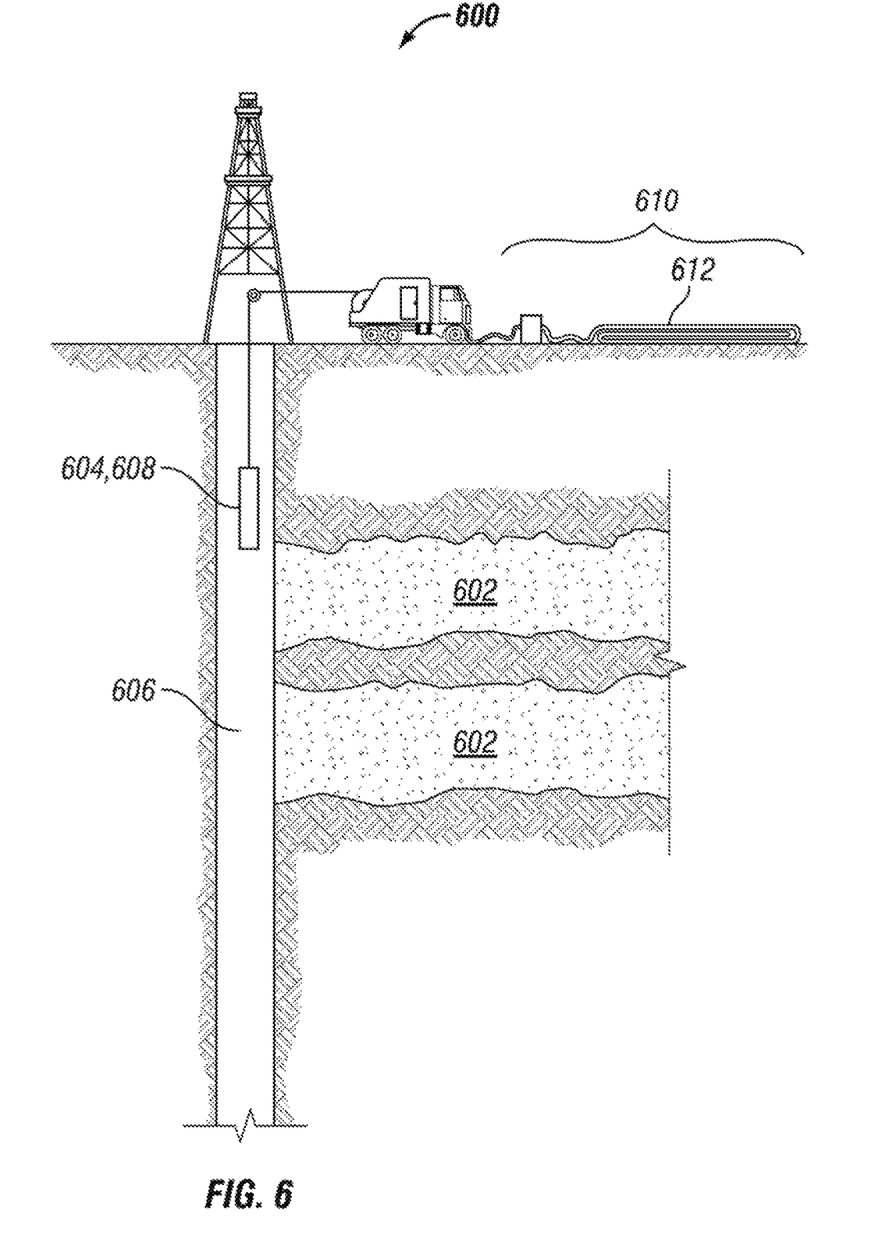
FIG. 6 shows a NMR system deployed as part of a wellbore and surface system in accordance with one embodiment of the present disclosure.
Figure 7:
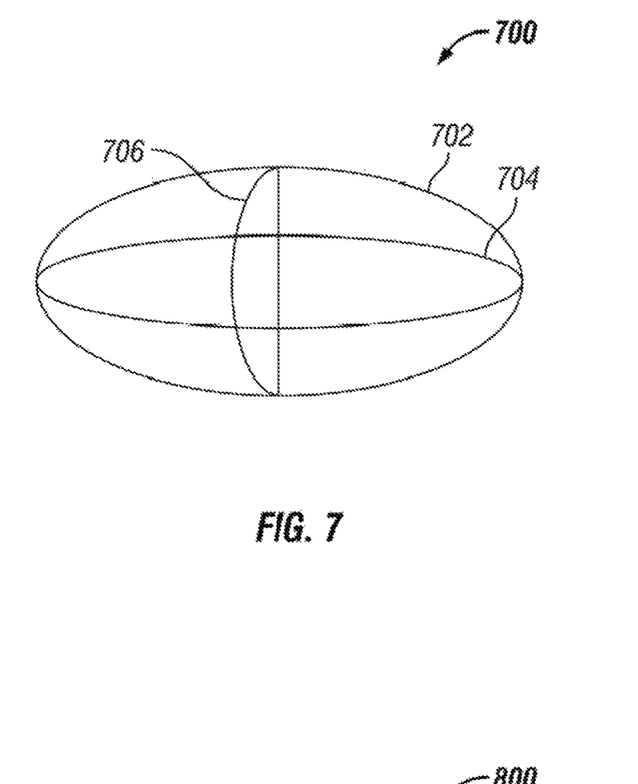
FIG. 7 shows a transmitter module with three transmitter coils in accordance with one embodiment of the present disclosure.

The present disclosure is not limited to the wellbore system and NMR system described in FIG. 5. Other configurations of the NMR system can also be used to determine the properties of subsurface formations. FIG. 6 shows a NMR system deployed as part of a wellbore and surface system 600 for investigating a subsurface formation 602 and determining properties of the subsurface formation. In this embodiment, the NMR receiver module 604 includes a three-axis feedback induction coil system that is deployed within a wellbore 606 as part of the wellbore tool 608. The NMR transmitter module 610 and the transmission coil 612 are deployed at the surface in the vicinity of the wellbore 606 (e.g., the wellbore can be within the cross section of the transmitter coil 612). At the surface, the transmitter module 610 may be larger and more powerful than the wellbore transmitter module. For example, the transmitter coil 612 may have 1-5 turns and a diameter of 5 to 100 meters (e.g., an area of 100 m$^2$). The transmitter coil 612 can be formed from a copper or aluminum cable. In some embodiments, the transmitter module 610 may also include three transmitter coils oriented in three different directions (e.g., the x-axis, the y-axis, and the z-axis). FIG. 7 shows a transmitter module 700 with three transmitter coils 702, 704, 706 oriented in three different orthogonal directions (e.g., the x-axis (702), the y-axis (704), and the z-axis (706)). Such a three-axis transmitter module can be used to improve position interrogation, to improve depth interrogation of formation properties, and to provide a three-dimensional magnetic field that may be manipulated in any desired direction. For example, this system can be used to produce an oscillating magnetic field of pulses that is perpendicular to the Earth's magnetic field and thus maximizes excitation efficiency at a detection volume. Also, the system 600 provides for a three-dimensional mapping of the formation 602 surrounding the wellbore 606. Such transmitter modules have been used previously as part of a controlled source audio magnetotelluric (CSAMT) system. In various embodiments, the three-axis transmitter module is useful for NMR applications because the surface based transmitter module can be moved at will and the three-component receiver can be positioned at various depths within the well. In various embodiments, the system 600 provides for three-dimensional data collection around the wellbore to a considerable depth. This three-dimensional data collection, in turn, provides for NMR imaging around a single well to a depth of at least a hundred meters (e.g., 500, 700, 900 meters).

Figure 8:
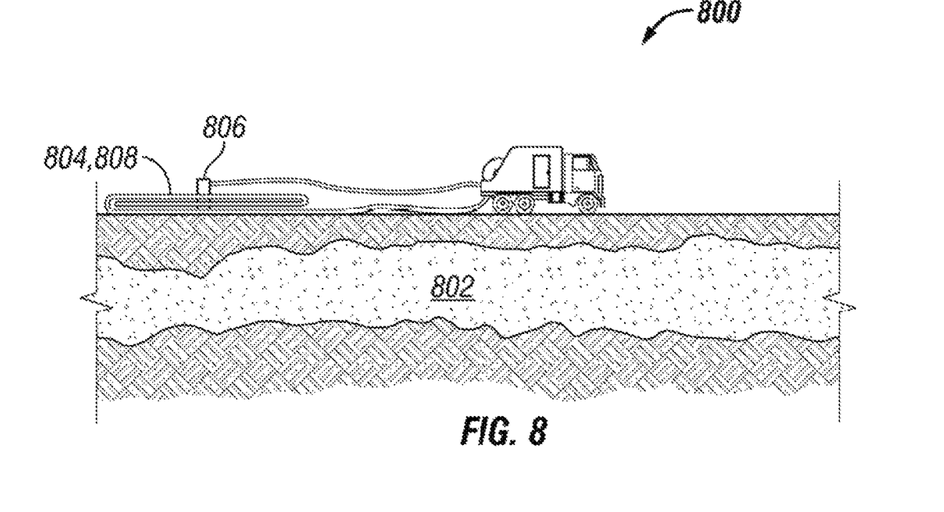
FIG. 8 shows one example of a NMR system deployed as part of a surface system in accordance with one embodiment of the present disclosure.

In another embodiment, both the NMR receiver module and the transmitter module are located at surface locations. FIG. 8 shows one example of a NMR system deployed as part of a surface system 800 for investigating a subsurface formation 802 and determining properties of the subsurface formation. In this case, an NMR transmitter module 804 is deployed at the surface and an NMR receiver module 806 that includes a three-axis feedback induction coil system is deployed within the cross section of the transmitter coil 808 or near the transmitter coil. In various embodiments, the three-axis feedback induction coil system described herein is smaller than past receiver coils, which had large cross sections (e.g., 30 to 100 meter diameters) in order to increase the sensitivity of the coils. The three-axis feedback induction coil system described herein can be laid out and operated with greater ease. For example, in some embodiments, one person can easily move these systems quickly to allow for multiple measurements, which can be used to achieve two-dimensional and three-dimensional imaging of the subsurface formation 802.

Figure 9:
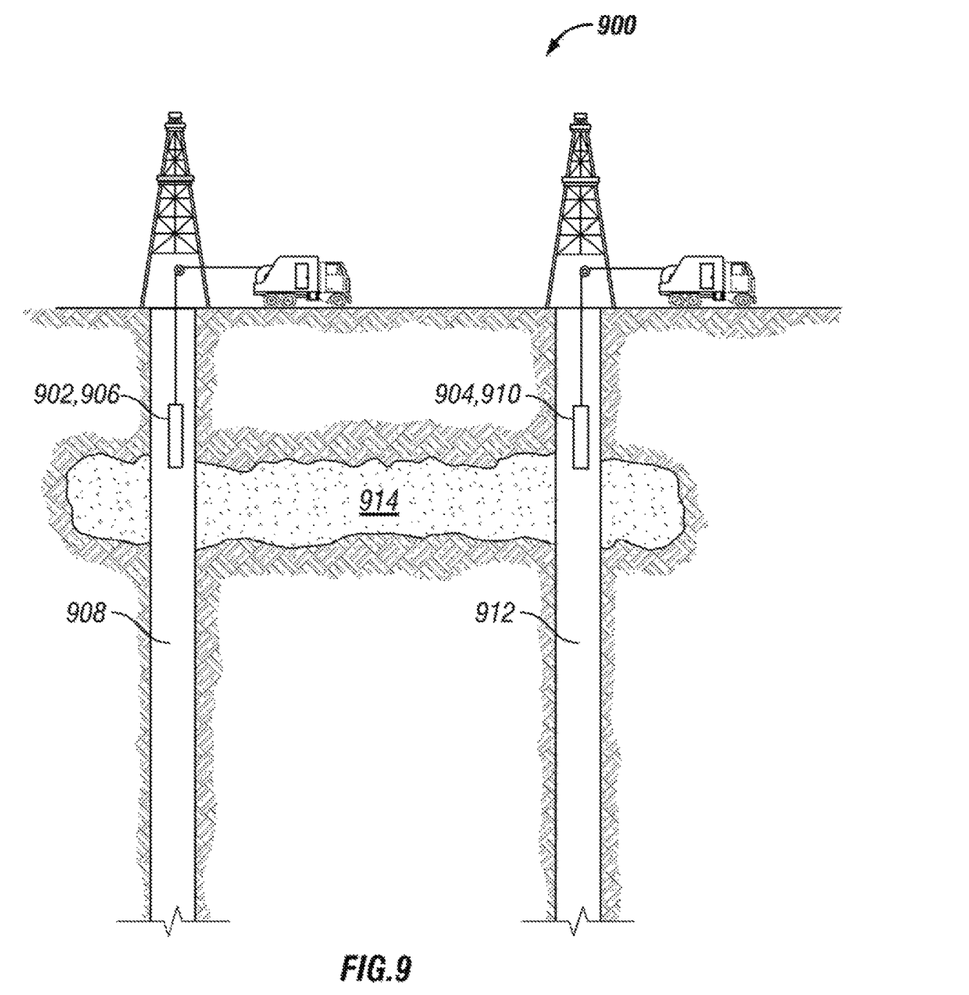
FIG. 9 shows an example of a cross-well system in accordance with one embodiment of the present disclosure.

In yet another embodiment, the NMR system is deployed as part of a cross-well system. FIG. 9 shows an example of a cross-well system 900 where a NMR transmitter module 902 and a NMR receiver module 904 are deployed in different wells. In such an embodiment, the NMR transmitter module 902 is deployed as part of a wellbore tool 906 in a first wellbore 908 and the NMR receiver module 904 with the three-axis feedback induction coil system is deployed as part of a second wellbore tool 910 in a second wellbore 912. The cross-well system can be used to determine the NMR properties of a formation area 914 between the two wellbores. The current amplitude and duration of the NMR pulse sequences applied by the NMR transmitter module 902 can be modulated based upon the distance between the two wellbores.

In one specific method for implementing the cross-well system. The NMR receiver module 904 in the second wellbore 912 is maintained at a first depth while the depth of NMR transmitter module 902 in the first wellbore 908 is varied. Then, the receiver module 904 is moved to a second depth and the depth of NMR transmitter module 902 in the first wellbore 908 is varied again. The process is repeated iteratively until an interval-of-interest is investigated. In this manner, the cross-well system 900 can determine NMR properties for the formation area 914 between the two wellbores and tomographically map that area to provide a two-dimensional NMR image of the area. In some embodiments, the inter-wellbore resistivity of the region can also be obtained separately and the resistivity could be used to distinguish oil and water filled porosity within the area.

Figure 10:
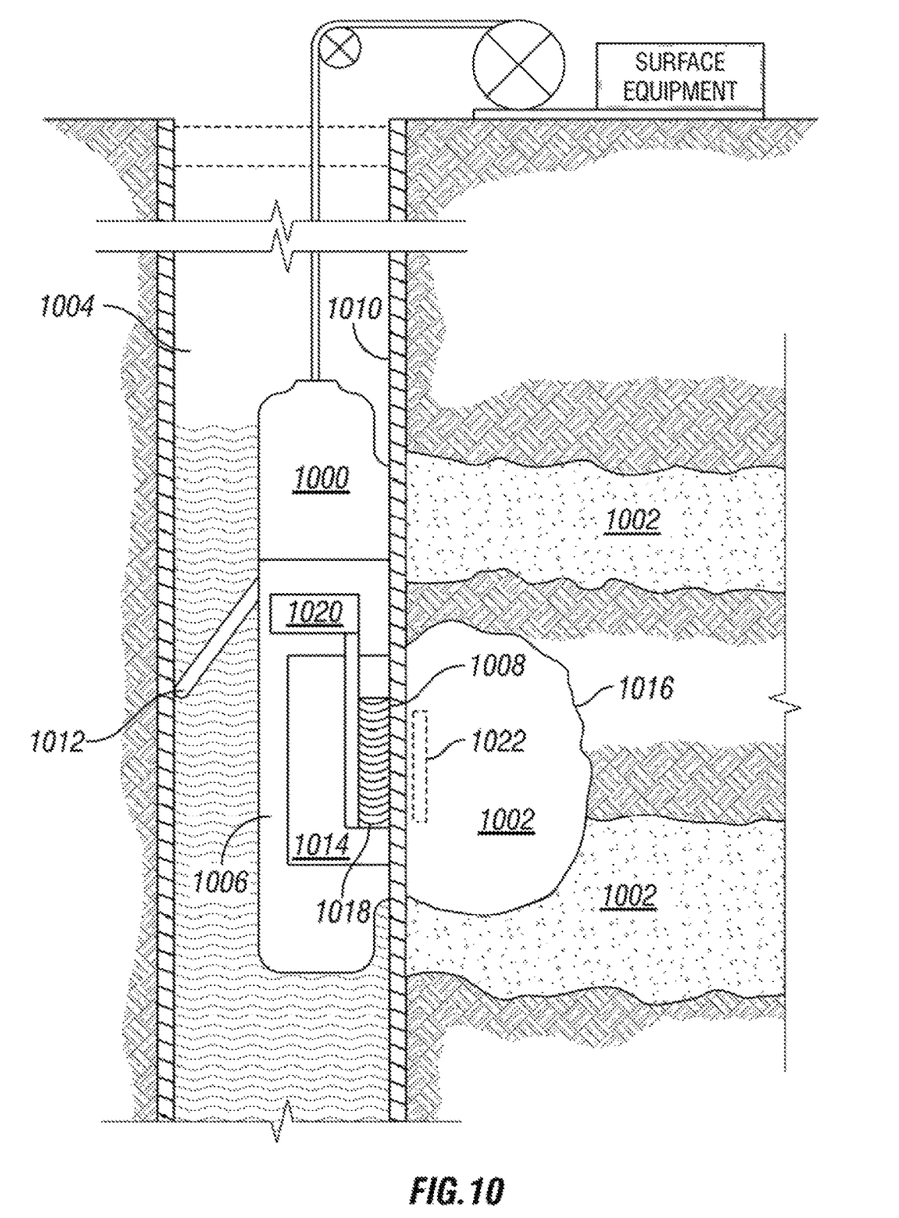
FIG. 10 shows a wireline logging tool in accordance with one embodiment of the present disclosure.

The NMR systems described herein may also use a feedback induction coil as both a transmitter coil and a receiver coil. FIG. 10 shows a wireline logging tool 1000 that uses a feedback induction coil for both applying NMR pulse sequences to a formation and detecting NMR signals that are generated within the formation. In particular, the wireline tool 1000 is used to investigate, in situ, a substance within a formation 1002 surrounding a wellbore 1004 to determine a property of the substance (e.g., properties of solids and liquids within the formation). The wireline tool 1000 includes an NMR logging module 1006 that is used to apply NMR pulse sequences to the formation and detect NMR signals generated within the formation. The NMR logging module includes a face 1008 that is shaped to contact the wellbore wall 1010 with minimal gaps or stand-off In some embodiments, a retractable arm 1012 is used to press the body of the wireline tool 1000 and the face 1008 against the wellbore wall 1010. The NMR logging module 1006 also includes an electro-magnetic device 1014 for applying a static magnetic field to a sensitivity zone 1016 within the formation. As explained above, in some embodiments, the electro-magnetic device 1014 is a magnet or an array of magnets formed from a magnetic material.

The NMR logging module 1006 also includes at least one feedback induction coil 1018 and NMR electronics 1020 electronically coupled to the coil (e.g., feedback electronics, transmitter, receiver, and spectrometer). The feedback induction coil 1018 includes a primary coil and a feedback coil. The primary coil of the feedback induction coil applies NMR pulse sequences to an area of interest 1022 within the formation. The area of interest is located within the sensitivity zone 1016 of the electro-magnetic device 1014. The static magnetic field and pulse sequences generate NMR signals within the area of interest 1022. These NMR signals are detected by the induction feedback coil 1018. The detected NMR signals are used to determine properties of the substance within the area of interest 1022. In various embodiments, the induction feedback coil 1018 increases the sensitivity of the wireline tool to the NMR signal, as compared to the sensitivity of past tools.

Figure 11:
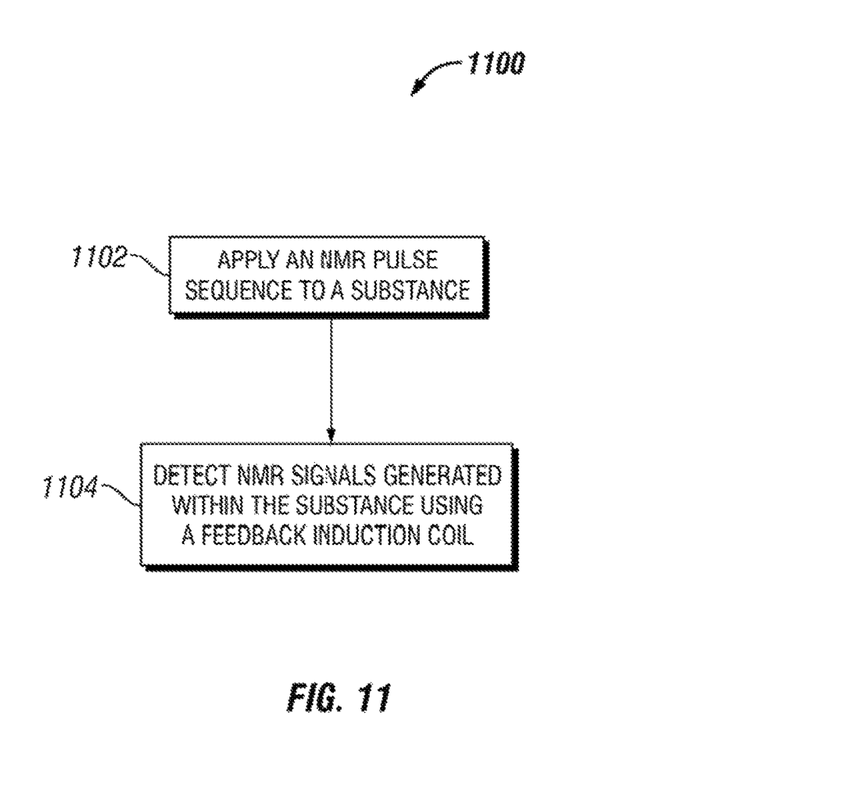
FIG. 11 shows a simplified method for analyzing a substance using NMR in accordance with one embodiment of the present disclosure.

FIG. 11 shows a simplified method 1100 for analyzing a substance using a nuclear magnetic resonance (NMR). The method begins at process 1102, which applies an NMR pulse sequence to the substance. In the case of a wireline logging operation, the NMR module is deployed on a wireline tool within a wellbore and the NMR pulse sequence is applied to a formation adjacent the wellbore. The method continues to process 1104, which detects NMR signals generated within the substance by the NMR pulse sequence using a feedback induction coil. The detected NMR signal can be used to determine NMR properties of the substance, such as $T_1$ relaxation time, $T_2$ relaxation time, and attenuation of the signal due to molecular diffusion. These NMR properties can be used to determine the properties of the substance itself. In the case of analyzing a formation, the NMR properties can be used to determine the porosity of the formation and also the composition of fluids within the formation.

The NMR systems and methods described herein are not limited to any device type or system. The NMR systems and methods described herein can be implemented in surface environments, such as in a laboratory or in subsurface environments. The systems and methods can be used in chemical production, food production, material inspection, and infrastructure inspection (e.g., building and bridges).

With respect to wellbore applications, the NMR systems and methods described herein are not limited to wireline systems, such as the ones shown in FIGS. 4, 5, 6, 9, and 10. For example, illustrative embodiments can also be used with any suitable means of conveyance, such coiled tubing. Various embodiments of the present disclosure may also be applied in logging-while-drilling (LWD) systems (e.g., a LWD tool) or measuring-while-drilling systems (e.g., MWD tools).

Although several example embodiments have been described in detail above, those skilled in the art will readily appreciate that many modifications are possible in the example embodiments without materially departing from the scope of this disclosure. Accordingly, all such modifications are intended to be included within the scope of this disclosure.

What is claimed is:

1. A nuclear magnetic resonance (NMR) system, the system comprising:
    an NMR transmitter that applies an NMR pulse sequence having a series of radio-frequency pulses to a substance; and
    an NMR receiver having a plurality of feedback induction coils configured to detect NMR signals generated within the substance in response to the NMR pulse sequence, wherein each of said plurality of feedback induction coils comprises a primary coil, a feedback coil, and feedback electronics (i) coupled to the primary coil and the feedback coil and (ii) configured to detect the NMR signals generated within the substance by applying a current to the feedback coil such that the current cancels a magnetic field through the primary coil produced by the NMR signals.

2. The system of claim 1, wherein said NMR transmitter includes a plurality of transmitter coils.

3. The system of claim 1, wherein said plurality of feedback induction coils are axially spaced from each other.

4. The system of claim 1, wherein said plurality of feedback induction coils include three orthogonally arranged feedback induction coils.

5. The system of claim 1, wherein said NMR transmitter includes three orthogonally arranged transmitter coils.

6. The system of claim 1, wherein said plurality of feedback induction coils include at least a first set and a second set of three orthogonally arranged feedback induction coils, said first set and said second set being axially spaced from each other.

7. The system of claim 1, further comprising:
    a wellbore tool comprising the NMR transmitter and the NMR receiver.

8. The system of claim 1, wherein the wellbore tool is a wireline tool.

9. The system of claim 1, further comprising:
    a wellbore tool comprising the NMR receiver; and
    a surface module comprising the NMR transmitter.

10. The NMR system of claim 1, further comprising:
    a surface module comprising the NMR receiver and the NMR transmitter.

11. The system of claim 5, wherein the substance is a geological formation having a surface and a wellbore traversing the formation, the NMR transmitter is movable on the surface, the NMR receiver is positionable at various depths in the formation, and the system is configured to provide three-dimensional data collection around the wellbore.

12. A method for analyzing a substance using nuclear magnetic resonance (NMR), the method comprising:
    applying an NMR pulse sequence to the substance wherein the NMR pulse sequence is comprised of a series of radio-frequency pulses; and
    detecting NMR signals generated by the NMR pulse sequence using an NMR receiver having a plurality of feedback induction coils, each of the plurality of feedback induction coils comprising a primary coil and a feedback coil, wherein the detecting comprises applying respective currents to each of the feedback coils such that the respective currents cancel magnetic fields through the respective primary coils produced by NMR signals generated by the substance in response to the NMR pulse sequence.

13. The method of claim 12, wherein the plurality of feedback induction coils are axially spaced from each other.

14. The method of claim 12, wherein the plurality of feedback induction coils include three orthogonally arranged feedback induction coils, and the NMR pulse sequence is applied using a transmitter module having three orthogonal transmitter coils.

15. The method of claim 14, wherein the substance is a geological formation, and the NMR receiver and the transmitter module are either (i) both located in a wellbore traversing the formation, or (ii) both located at a surface location of the formation, or (iii) located with the NMR receiver located in a wellbore traversing the formation and the transmitter module located at a surface location of the formation.

16. The method of claim 15, further comprising:
    moving the NMR transmitter module on the surface of the formation and applying the NMR pulses at different locations along the surface;
    positioning the NMR receiver at various depths in the wellbore and detecting NMR signals generated by the NMR pulse sequence at those depths; and
    collecting three-dimensional data around the wellbore and providing NMR imaging of the formation at a depth in the formation away from the wellbore.

17. The method of claim 12, further comprising:
    from said NMR signals detected by the NMR receiver having a plurality of feedback induction coils, collecting three-dimensional data around the wellbore; and
    utilizing said three-dimensional data, providing NMR imaging of the formation at a depth in the formation away from the wellbore.

18. A wellbore tool comprising:
    an NMR transmitter that applies an NMR pulse sequence having a series of radio-frequency pulses to a substance; and an NMR receiver having a plurality of feedback induction coils configured to detect NMR signals generated within the substance in response to the NMR pulse sequence, wherein each of said plurality of feedback induction coils comprises a primary coil, a feedback coil, and feedback electronics (i) coupled to the primary coil and the feedback coil and (ii) configured to detect the NMR signals generated within the substance by applying a current to the feedback coil such that the current cancels a magnetic field through the primary coil produced by the NMR signals.

19. The wellbore tool of claim 18, wherein said plurality of feedback induction coils are axially spaced from each other.

20. The wellbore tool according to claim 18, wherein the plurality of feedback induction coils include three orthogonally arranged feedback induction coils, and the NMR transmitter includes three orthogonal transmitter coils.

* * * * *